United States Patent [19]

Hitomi et al.

[11] Patent Number: 5,643,267
[45] Date of Patent: Jul. 1, 1997

[54] BONE CONNECTOR ADAPTED FOR JOINING CUT BONE ENDS

[75] Inventors: Shigeki Hitomi, Osaka-fu; Hiroshi Mizuno, Kyoto-fu; Satoshi Ojima, Tokyo, all of Japan

[73] Assignee: Asahi Kogaku Kogyo Kabushiki Kaisha, Tokyo, Japan

[21] Appl. No.: 396,577

[22] Filed: Mar. 1, 1995

Related U.S. Application Data

[63] Continuation of Ser. No. 28,196, Mar. 9, 1993, abandoned.

[30] Foreign Application Priority Data

Mar. 10, 1992 [JP] Japan ................... 4-087756
May 21, 1992 [JP] Japan ................... 4-155754

[51] Int. Cl.$^6$ ........................... A61B 17/86
[52] U.S. Cl. ................ 606/73; 411/389; 24/694
[58] Field of Search ................. 623/16; 606/73, 606/74, 64, 69, 89, 62; 24/31 C, 694; 411/383, 388, 389

[56] References Cited

U.S. PATENT DOCUMENTS

| | | | |
|---|---|---|---|
| 64,654 | 5/1867 | Floyd | 403/361 |
| 1,644,477 | 10/1927 | Klaus | 411/389 |
| 1,897,196 | 2/1933 | Hunt | 411/389 |
| 3,488,779 | 1/1970 | Christensen | 623/16 X |
| 4,016,874 | 4/1977 | Maffei et al. | 606/62 |
| 4,158,895 | 6/1979 | Reswick et al. | 623/16 |
| 4,456,005 | 6/1984 | Lichty | 606/73 X |
| 4,467,794 | 8/1984 | Maffei et al. | 606/62 |
| 4,682,590 | 7/1987 | Kothmann | 606/62 |
| 4,798,585 | 1/1989 | Inoue et al. | |
| 4,938,768 | 7/1990 | Wu | 623/16 |
| 4,946,378 | 8/1990 | Hirayama et al. | |
| 4,969,913 | 11/1990 | Ojima | |
| 5,074,879 | 12/1991 | Pappas et al. | 623/18 |
| 5,108,398 | 4/1992 | McQueen et al. | 606/62 |
| 5,128,146 | 7/1992 | Hirayama et al. | |
| 5,147,361 | 9/1992 | Ojima et al. | |
| 5,169,400 | 12/1992 | Muhling et al. | 606/73 |
| 5,346,501 | 9/1994 | Regula et al. | 606/151 |

FOREIGN PATENT DOCUMENTS

| | | | |
|---|---|---|---|
| 0472727 | 4/1951 | Canada | 411/388 |
| 0584029 | 1/1977 | Switzerland | 433/190 |
| 1692566 | 11/1991 | U.S.S.R. | 606/62 |

*Primary Examiner*—David H. Willse
*Attorney, Agent, or Firm*—Greenblum & Bernstein P.L.C.

[57] ABSTRACT

A bone connector including a first joint which is inserted and secured in one of cut bone pieces to be interconnected at the cut end thereof, a second joint which is inserted and secured in the other bone piece at the cut end thereof, and engaging portions provided on the first and second joints to connect the same.

26 Claims, 10 Drawing Sheets

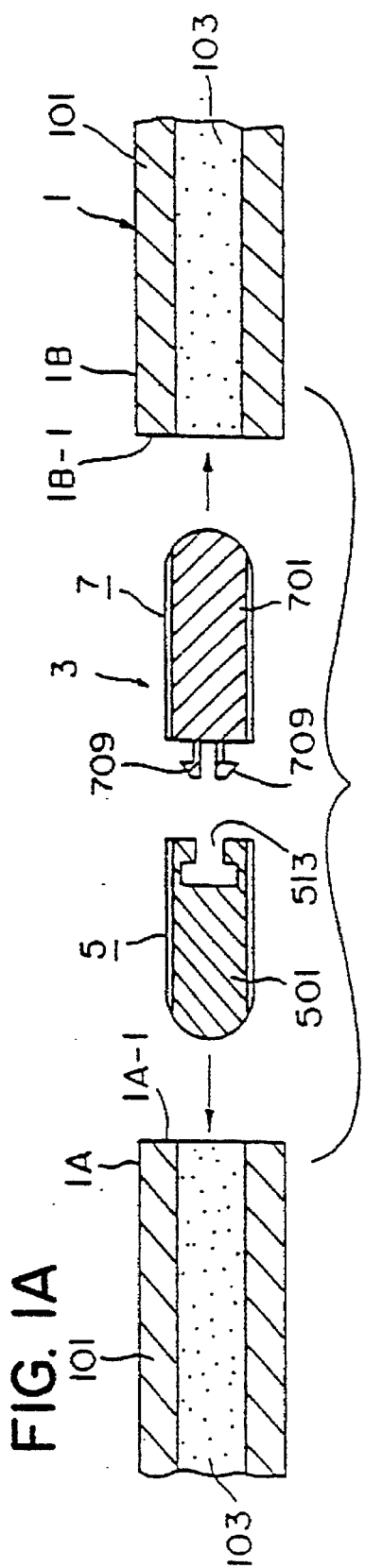
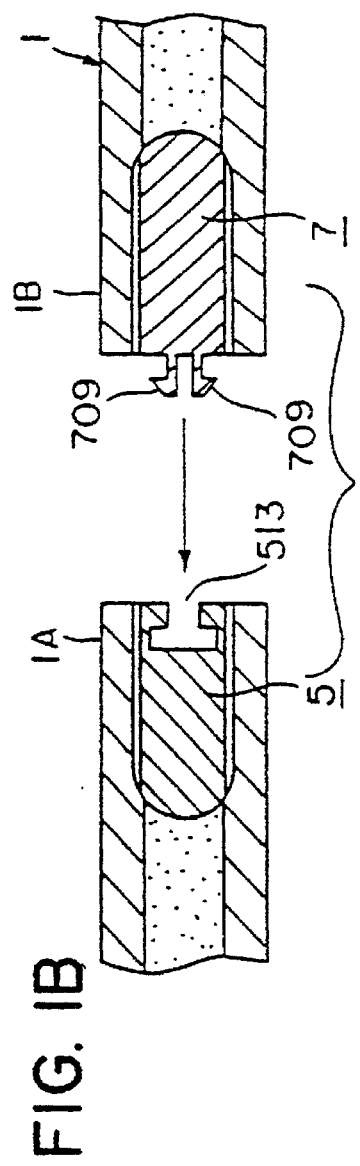
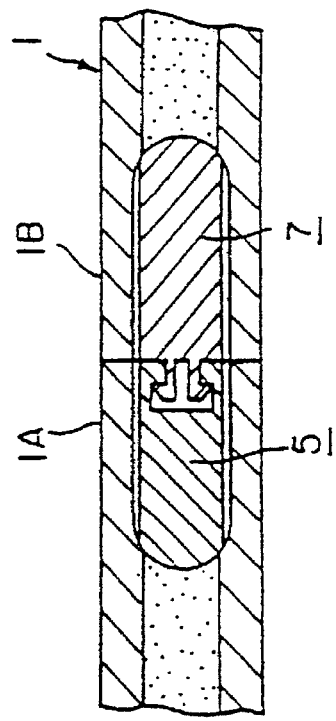
FIG. 1A
FIG. 1B
FIG. 1C

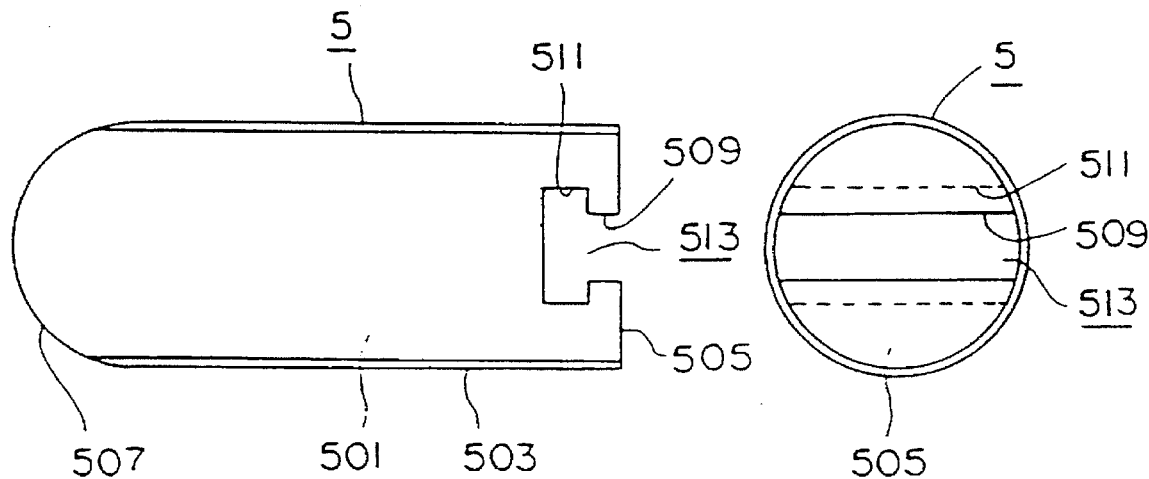
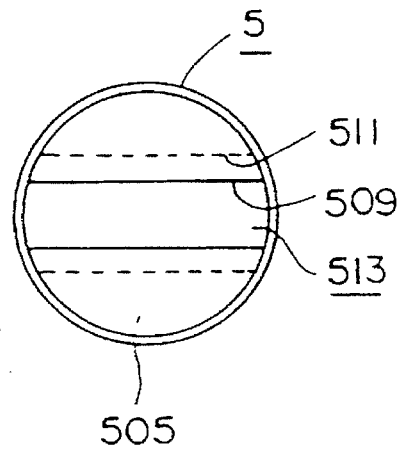
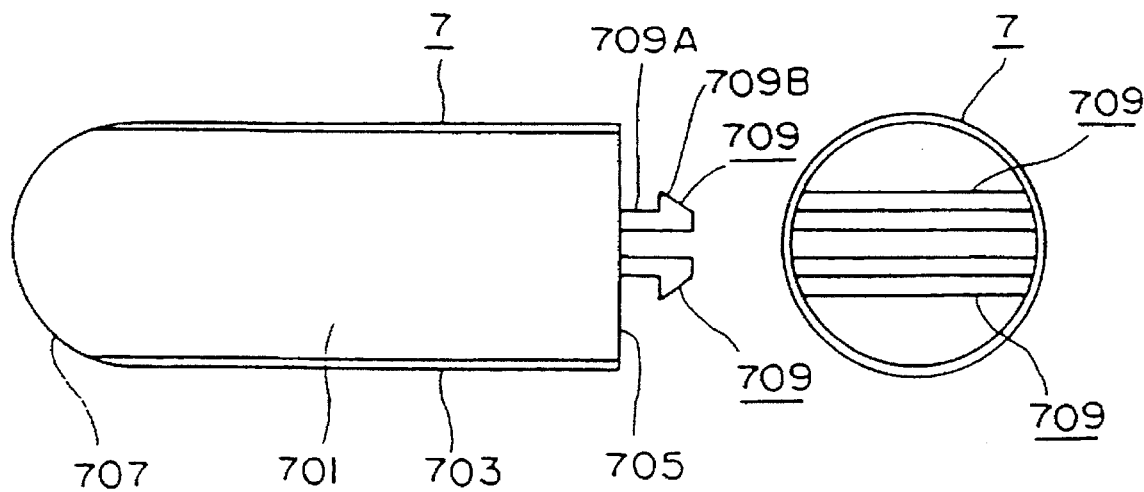
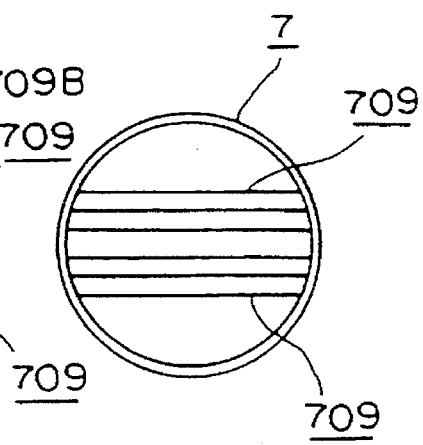

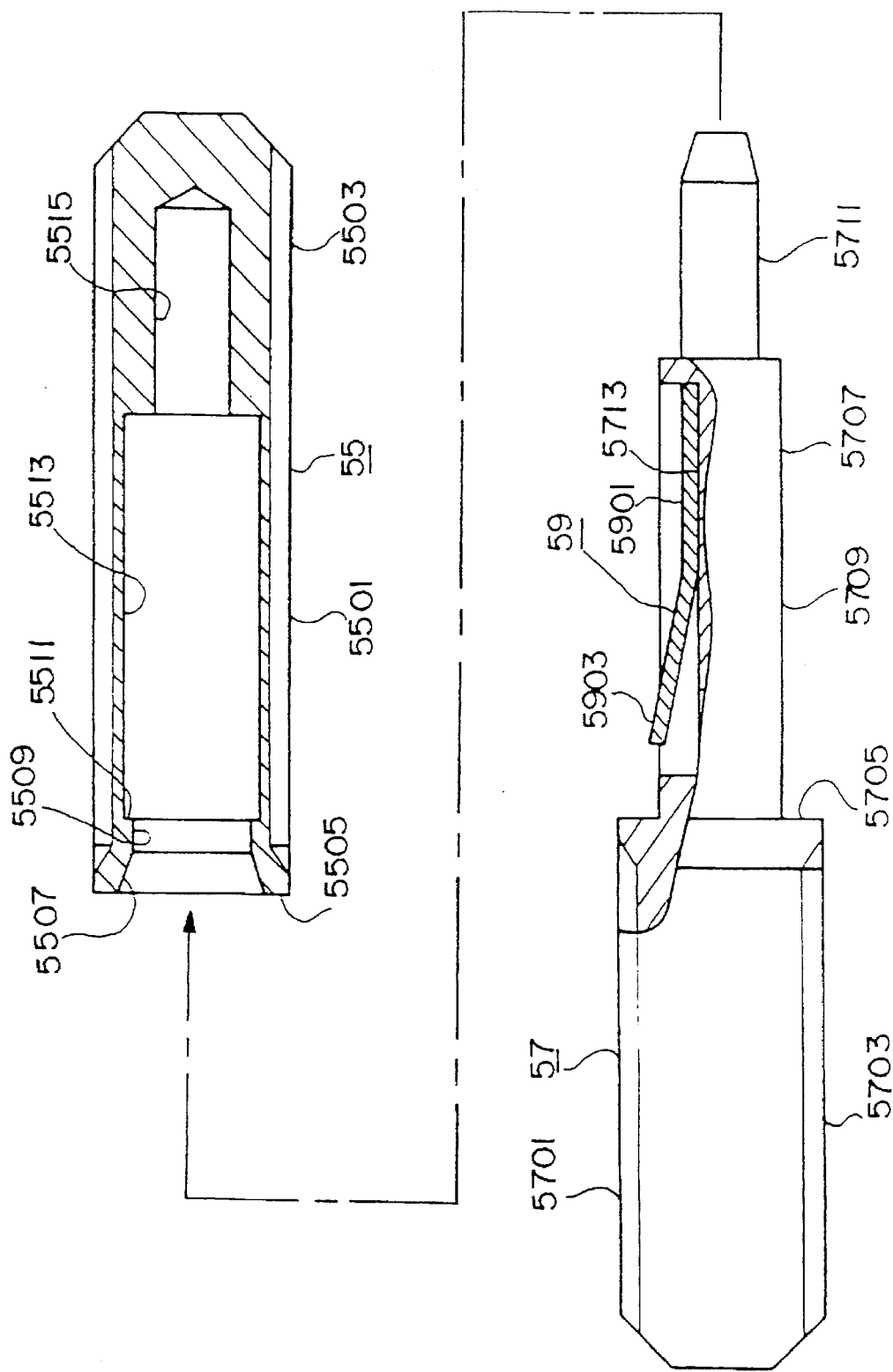

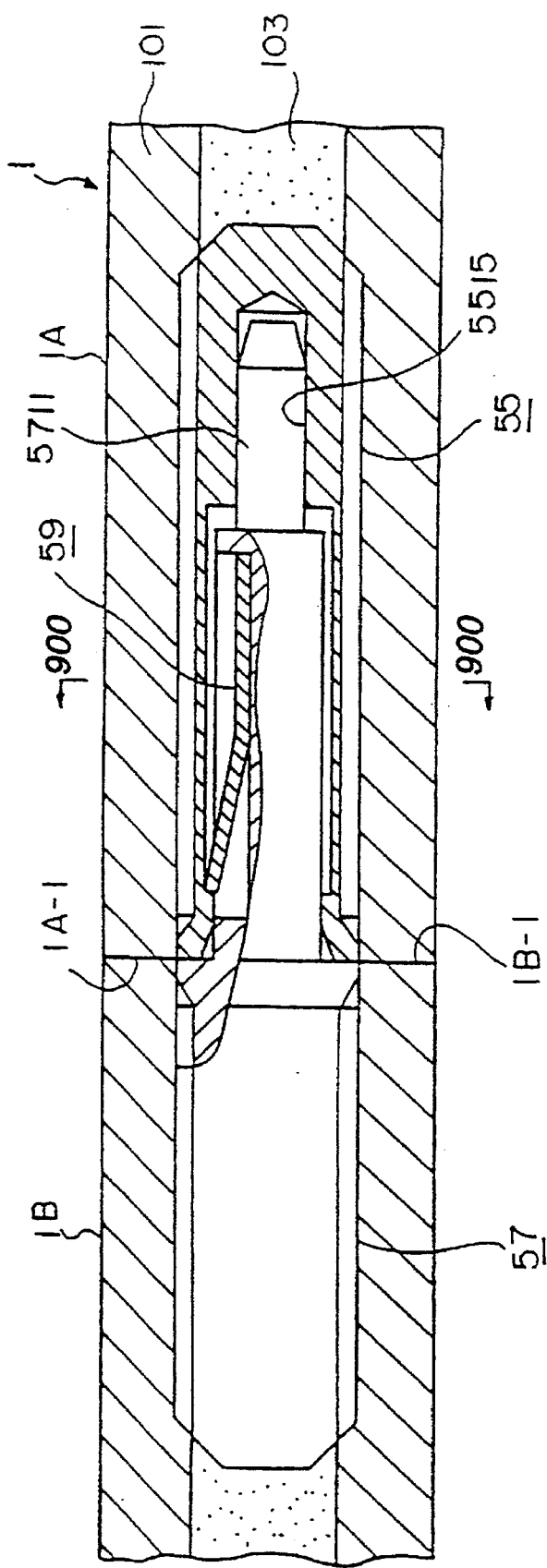
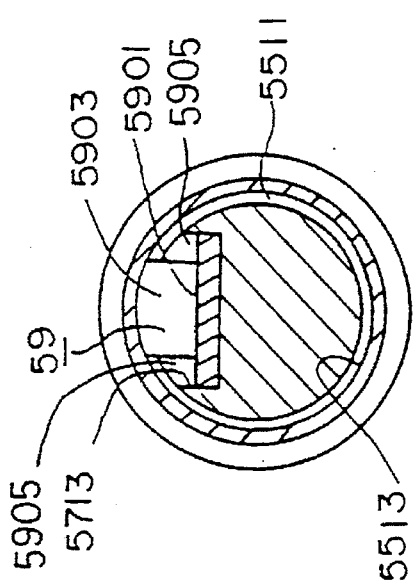

BONE CONNECTOR ADAPTED FOR JOINING CUT BONE ENDS

This application is a continuation of application Ser. No. 08/028,196, filed Mar. 9, 1993, now abandoned.

BACKGROUND OF THE INVENTION

1. Field of the Invention

The present invention relates to a bone connector which is adapted to connect cut bone pieces.

2. Description of Related Art

For instance, in a surgical operation of the chest for exposing the lungs and the heart, for example, a part of the ribs is usually cut and temporarily removed. After the surgical operation is completed, a piece of bone cut from the rib (referred to as a bone piece) is reconnected to the associated rib.

To connect the cut ends of a bone piece and the associated rib, a wire (or biedegradable thread), or a metal or plastic connecting plate is normally used. When the connecting with wire, a ceramic pin is inserted in the marrow of the bone piece at the cut end thereof initially. Then, a through hole is pierced in the vicinity of the cut end of the rib. Consequently, the cut end of the rib can be bound by the wire or the thread which is tied to the ceramic pin. The insertion of the ceramic pin and the tying and stringing operations are troublesome, however. Moreover, it is necessary to strip a substantial part of the intercostal muscles in the vicinity of the cut ends of the ribs, which both burdens a patient during the operation and increases recovery time.

When connecting with a metal or plastic connecting plate, holes are pierced in the cut ends of both the bone piece and the associated rib, so that the connecting plate which lies along the outer surfaces of the bone piece and the associated rib is secured to the bone piece and the associated rib by securing pins which are inserted in the connecting plate and the holes of the bone piece and the associated rib to connect the bone piece and the associated rib.

In this method, it is also necessary to strip a substantial part of intercostal muscles in the vicinity of the cut ends of the ribs. Furthermore, the metal plate is heavy, and accordingly, increases the burden on a patient; and the plastic plate has less biocompatibility or bioaffinity with the surrounding tissue of the cut ends of the ribs.

SUMMARY OF THE INVENTION

The primary object of the present invention is to eliminate the drawbacks mentioned above by providing a bone connector which can easily connect the bone ends while minimizing the burden on a patient and which has a good biocompatibility or bioactive affinity with the tissue.

To achieve the object mentioned above, according to the present invention, there is provided a bone connector comprising a first joint which is inserted and secured in the cut end of one of the cut bone pieces to be interconnected, a second joint which is inserted and secured in the cut end of the other cut bone piece to be interconnected, and engaging portions provided on the first and second joints to connect the same.

According to another aspect of the present invention, there is provided a bone connector comprising first and second joints which are secured to cut ends of bone pieces to be interconnected, engaging portions provided on the first and second joints to connect the same, and an elastically deformable spring member which is restored when the engagement of the engaging portions is completed to lock the engagement.

According to still another aspect of the present invention, a bone connector comprises a first joint which is secured to a cut end of one of the bone pieces to be interconnected, and a second joint which is secured to a cut end of the other bone piece, wherein said first joint is provided with a first body which can be embedded and secured in the cut end of said one bone piece, and a first engaging portion provided on the first body; said second joint is provided with a second body which can be embedded and secured in the cut end of said the other bone piece, and a second engaging portion provided on the second body and being engaged by the first engaging portion, so that when the engagement of the first engaging portion and the second engaging portion is established, the cut ends of the bone pieces are held in a close surface contact; said first and second joints are made of a material strong enough to hold a close surface contact of the cut ends of the bone pieces; said first and second bodies are coated at least at the outer surfaces thereof with a material which is assimilative to or has a bioactive affinity with the tissue.

The present disclosure relates to subject matter contained in Japanese patent applications Nos. 4-87756 (filed on Mar. 10, 1992) and 4-155754 (filed on May 21, 1992) which are expressly incorporated herein by reference in their entirety.

BRIEF EXPLANATION OF THE DRAWINGS

The invention will be described below in detail with reference to the accompanying drawings, in which;

FIGS. 1A through 1C are explanatory views of a connecting operation of cut ribs, using a bone connector according to the present invention;

FIGS. 2A and 2B are a side elevation view and a front elevation view of a first joint of a bone connector according to a first embodiment of the present invention, respectively;

FIGS. 3A and 3B are a side elevation view and a front elevation view of a second joint of a bone connector according to a first embodiment of the present invention, respectively;

FIG. 10 is a side elevation view of first and second joints of a bone connector according to a fifth embodiment of the present invention;

FIG. 11A is a side elevation view of first and second joints of a bone connector in an assembled state, according to a fifth embodiment of the present invention; and, FIG. 11B is a sectional view taken along the line 900—900 in FIG. 11A; and, FIGS. 12A and 12B are a top view and a side elevation view of a spring according to a fifth embodiment of the present invention.

DESCRIPTION OF THE PREFERRED EMBODIMENT

Figure 4A:
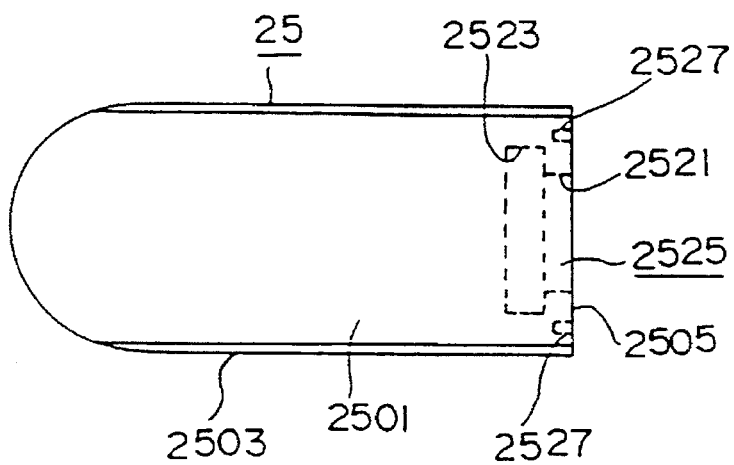
FIGS. 4A and 4B are a side elevation view and a front elevation view of a first joint of a bone connector according to a second embodiment of the present invention, respectively.

FIGS. 1A through 1C illustrate a process for connecting cut rib pieces. A rib 1 is cut at an intermediate portion in a direction perpendicular to the longitudinal axis thereof. One of the cut ribs is indicated at 1A (first bone piece) and the other at 1B (second bone piece). The rib 1 consists of an outer cortex bone portion 101 and a center (inner) marrow 103.

A bone connector 3 according to the present invention includes a first joint 5 which is secured to the cut end of the first bone piece 1A and a second joint 7 which secured to the cut end of the second bone piece 1B.

The first joint 5 has a circular rod body 501 of predetermined length which is inserted and secured in the first bone piece 1A and which is provided, on the outer peripheral surface thereof, with a thread (male screw) 503, as shown in FIGS. 2A and 2B. The rod body 501 has a flat outer end 505 which is flush with the end surface 1A-1 of the first bone piece 1A when the first joint 5 is fitted in the first bone piece 1A, and a semi-spherical inner end 507. The rod body 501 is provided, on the outer end 505 thereof, with a stepped engaging groove 513 comprising a groove 509 of smaller width, and a groove 511 of larger width. The engaging groove 513 extends through the outer end 505 in a direction perpendicular to the longitudinal axis of the rod body 501. In the first embodiment, the engaging groove 513 comprises an engaging portion of the first joint 5.

The second joint 7 has a circular rod body 701 of predetermined length which is inserted and secured in the second bone piece 1B and which is provided, on the outer peripheral surface thereof, with a thread (male screw) 703, similar to that of the first joint 5, as can be seen in FIGS. 3A and 3B. The rod body 701 has a flat outer end 705 which is flush with the end surface 1B-1 of the second bone piece 1B when the second joint 7 is fitted in the second bone piece 1B, and a semi-spherical inner end 707. The rod body 701 is provided on the outer end 705 thereof, with a pair of engaging projections 709 which can be engaged in the engaging groove 513 of the first joint 5. Each engaging projection 709 has a leg 709A to be fitted into the small groove 509 of the first joint, and a projection 709B which projects from the front end of the leg 709A to be fitted in the large groove 511 of the first joint. In the illustrated embodiment, the engaging projections 709 constitute an engaging portion of the second joint 7.

When the engaging projections 709 of the second joint 7 are fitted in the engaging groove 513 of the first joint 5, the flat end surfaces 505 and 705 of the first and second joints 5 and 7 are flush with each other. The contact is retained by the engagement of the engaging projections 709 and the engaging groove 513.

The first and second joints 5 and 7 are made of, for example, titanium, stainless steel, titanium alloy, etc., and are coated with apatite at the outer surface thereof.

To connect the cut rib 1, i.e., the first and second bone pieces 1A and 1B, the rod body 501 of the first joint 5 is inserted in the marrow 103 and screwed into the cortical bone portion 101 of the first bone piece 1A from the end surface 1A-1, for example, by rotating a screw driver (minus driver) which is fitted in the small width groove 509 of the first joint 5. Similarly, the rod body 701 of the second joint 7 is inserted in the marrow 103 and screwed into the cortical bone portion 101 of the second bone piece 1B from the end surface 1B-1, for example, by rotating a screw driver (minus driver) which is inserted between the engaging projections 709. The first and second joints 5 and 7 are screwed into the first and second bone pieces 1A and 1B until the end surfaces 505 and 705 of the first and second joints 5 and 7 are flush with the end surfaces 1A-1 and 1B-1 of the first and second bone pieces 1A and 1B, respectively, as shown in FIG. 1B. Consequently, the threaded outer peripheral surfaces and 703 of the first and second joints 5 and 7 are screw-engaged in the cortical bone portion 101 of the first and second bone pieces 1A and 1B, so that the first and second joints 5 and 7 are secured to the first and second bone pieces 1A and 1B, respectively.

Thereafter, the first and second bone pieces 1A and 1B are moved towards each other to move the opposed end surfaces 1A-1 and 1B-1 thereof close to each other, so that the engaging projections 709 of the second joint 7 are inserted in the groove 509 of the first joint 5 while being elastically deformed. As soon as the engaging projections 709 of the second joint 7 move past small groove 509 into large groove 511 of the first joint, the engaging projections 709 are restored to their original shape due to elastic restoring force, so that the engaging projections 709 are snugly fitted in the large groove 513. Consequently, the surfaces 505 and 705 of the first and second joints 5 and 7 and the surfaces 1A-1 and 1B-1 of the first and second bone pieces 1A and 1B are flush with each other, respectively, as shown in FIG. 1C.

According to the present invention discussed above, the connecting operation of a pair of bone pieces 1A and 1B can be simplified in comparison with the connection using the wire or biodegradable thread in the prior art. Furthermore, according to the present invention, the necessity for separating or stripping of the intercostal muscles can be minimized.

The first and second joints 5 and 7 can be made of a material having a rigidity strong enough to retain the close contact of the surfaces of the first and second bone pieces 1A and 1B. Preferably, the first and second joints 5 and 7 are made of a light titanium alloy, so that an artifact is not produced by the bone connector during CT photography. In addition, the joints 5 and 7 made of a light titanium alloy are sufficiently strong, yet sufficiently light to minimize the burden on a patient.

Furthermore, the first and second joints 5 and 7 are coated with apatite, and have no problem with assimilation to or bioactive affinity with the body.

Since the bone tissues of the first and second bone pieces 1A and 1B to be connected come into direct contact with each other, the bone tissues will interconnect easily.

Figure 4B:
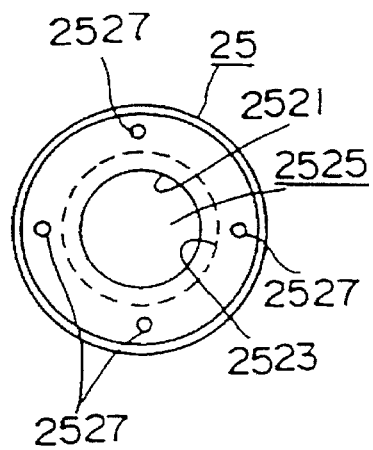
Figure 5A:
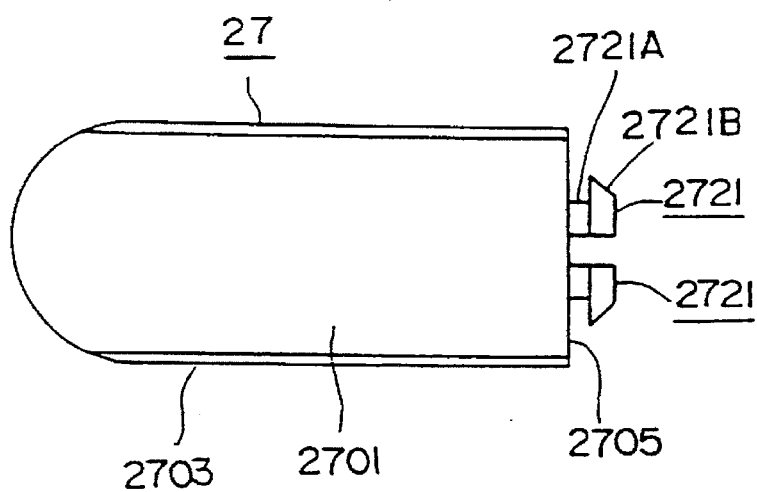
FIGS. 5A and 5B are a side elevation view and a front elevation view of a second joint of a bone connector according to a second embodiment of the present invention, respectively.
Figure 5B:
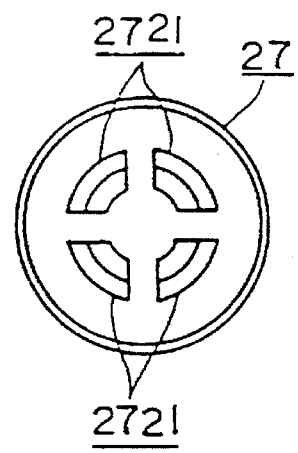

FIGS. 4 and 5 show a second embodiment of the present invention. The engaging grooves and projections of the first and second joints 25 and 27 in the second embodiment differ in shape from those of the first embodiment.

The first joint 25 has a rod body 2501 which is provided on the outer peripheral surface thereof with a threaded portion (male screw) 2503. The rod body 2501 has a flat outer end surface 2505 which is provided with a small diameter center circular recess 2521 and a larger diameter circular recess 2523 which is coaxial to and connected to the center circular recess 2521. The recesses 2521 and 2523 constitute an engaging groove 2525.

The end surface 2505 is provided with four bottomed holes 2527 which are angularly spaced from each other in the vicinity of the outer peripheral surface thereof. A jig or tool which is adapted to screw the first joint 25 into the first bone piece 1A is engaged in the holes 2527.

The second joint 27 has a rod body 2701 which is provided, on the outer peripheral surface thereof, with a threaded portion (male screw) 2703. The rod body 2701 has a flat outer end surface 2705 which is provided thereon with four engaging projections 2721 which can be fitted in the engaging groove 2525. The engaging projections 2721 are spaced from one another, so that a jig (plus or minus screw driver, etc.) can be fitted therebetween to screw the second joint 27 into the second bone piece 1B.

Each engaging projection 2721 has a leg 2721A to be fitted into the small diameter circular recess 2521 of the first joint and a projection 2721B which projects from the front end of the leg 2721A to be fitted in the larger diameter circular recess 2523 of the first joint.

When the engaging projections 2721 of the second joint 27 are fitted in the engaging groove 2525 of the first joint 25, the flat end surfaces 2505 and 2705 of the first and second joints 25 and 27 are flush with each other. The surface contact is retained by the engagement of the engaging projections 2721 and the engaging groove 2525. Thus, the same technical effects as those in the first embodiment can be expected from the second embodiment.

Figure 6:
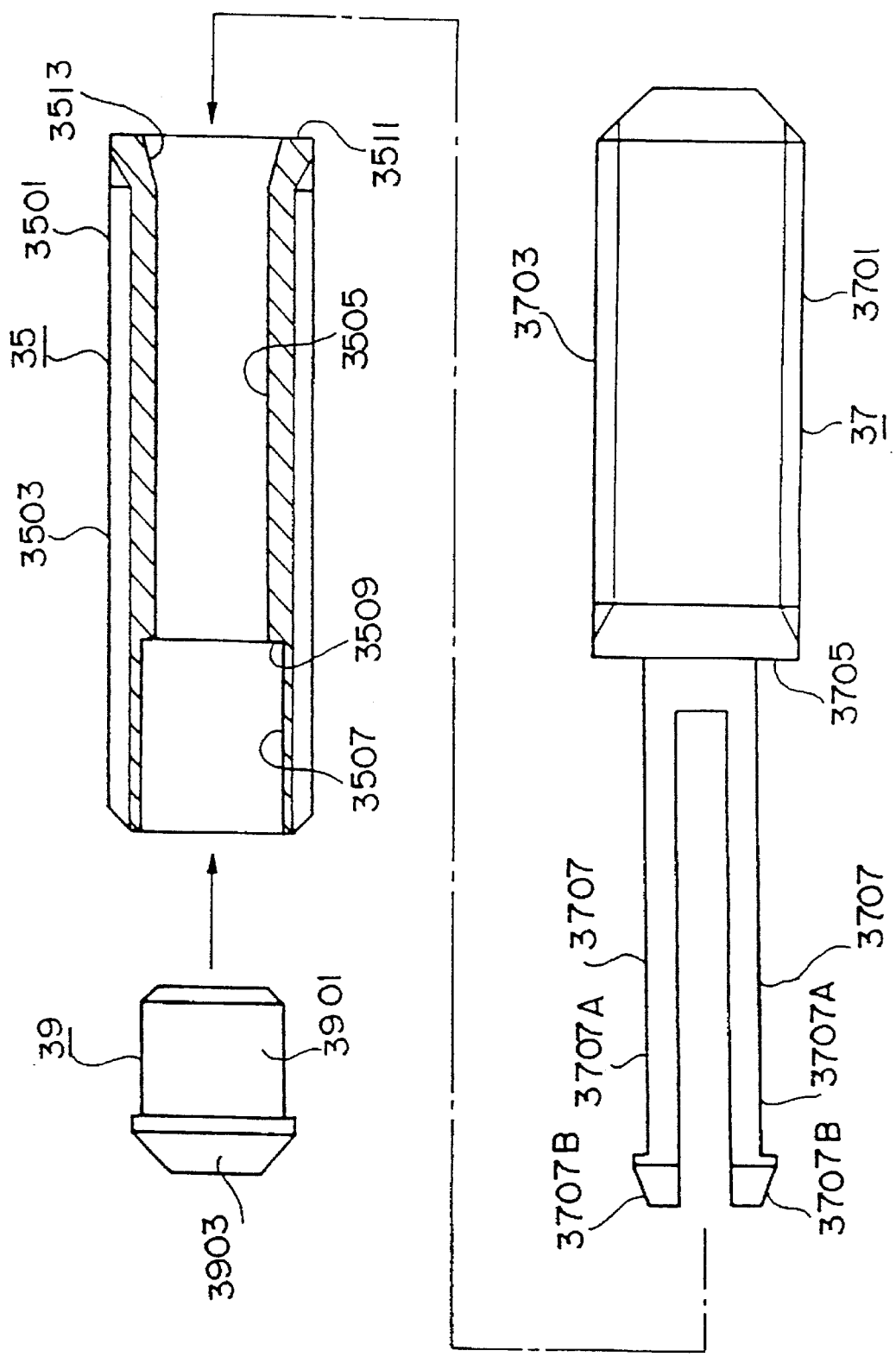
FIG. 6 is a side elevation view of first and second joints of a bone connector according to a third embodiment of the present invention.
Figure 7:
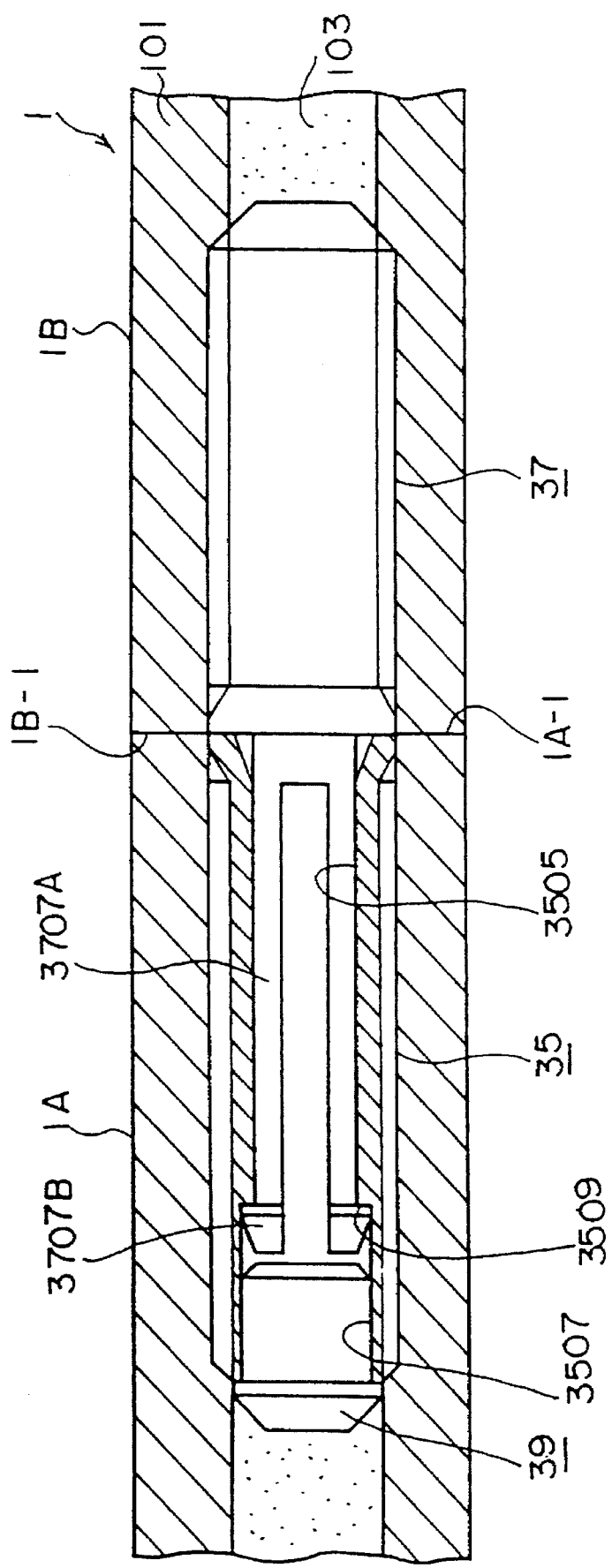
FIG. 7 is a side elevation view of first and second joints of a bone connector in an assembled state, according to a third embodiment of the present invention.

FIGS. 6 and 7 show a third embodiment of the present invention. In the third embodiment, the first joint 35 has a hollow cylindrical body 3501 of predetermined length which is provided on the outer peripheral surface thereof with a threaded portion (male screw) 3503. The hollow portion of the cylindrical body 3501 consists of a small diameter circular hole 3505 and a larger diameter circular hole 3507 coaxial thereto. The small circular hole 3505 and the large circular hole 3507 are connected to each other by a shoulder portion 3509. The small circular hole 3505, the large circular hole 3507, and the shoulder portion 3509 comprise an engaging portion of the first joint 35.

The small diameter circular hole 3505 is provided on the end opposite the shoulder portion 3509, with a conically tapered opening 3513 whose diameter gradually increases towards the open end thereof. The conical opening 3513 terminates at an annular end surface 3511 which is flush with the end surface 1A-1 of the first bone piece 1A when the first joint 35 is correctly inserted in the first bone piece 1A.

The other open end of the large circular hole 3507 is closed by a plug 39 fitted therein. The plug 39 has a circular rod body 3901 to be inserted in the large circular hole 3507 and a head 3903 which abuts against the open end of the cylindrical body 3501 of the first joint 35 when the plug 39 is inserted in the first joint 35. The outer diameter of the head 3903 is substantially identical to or smaller than the root diameter of the thread 3503, as can be seen in FIG. 7. The front end of the head 3903 is tapered in a truncated conical shape.

The second joint 37 has a circular rod body 3701 of predetermined length which is provided on the outer peripheral surface thereof with a threaded portion (male screw) 3703. The rod body 3701 has a flat end surface 3705 which is provided thereon with a plurality of engaging projections 3707. The annular flat end surface 3705 of the rod body 3701 is flush with the flat end surface 1B-1 of the second bone piece 1B when the second joint 37 is fitted in the second bone piece 1B. The other end of the rod body 3701 is conically tapered.

The engaging projections 3707 which are circumferentially spaced from one another can be made of separate pieces or a cylinder or bar which is axially slit in a plurality of radial directions.

Each engaging projection 3707 has a leg 3707A and a projection 3707B which projects from the front end of the leg 3707A. The diameter of an imaginary circle defined by the legs 3707A corresponds to the inner diameter of the small circular hole 3505. The engaging projections 3707 correspond to the engaging portion in the second embodiment.

The dimensions of the circular holes 3505 and 3507 and the shoulder portion 3509 are such that when the legs 3707A are inserted in the small circular hole 3505 while being elastically deformed, and come to the large circular hole 3507, the projections 3707B are snugly fitted in the portion of the large circular hole 3507 that is defined between the plug 39 and the shoulder portion 3509. In this state, the projections 3707B abut against the shoulder portion 3509, and the surfaces 3511 and 3705 of the first and second joints 35 and 37 are flush with each other.

According to the third embodiment shown in FIGS. 6 and 7, in addition to the technical effects achieved by the previous embodiments, the first and second joints 35 and 37 can be coaxially held along a line by the engagement of the legs 3707A and the small circular hole 3505, and accordingly, the first and second bone pieces 1A and 1B can be accurately aligned, thus resulting in an optimal recovery of the ribs.

Figure 8:
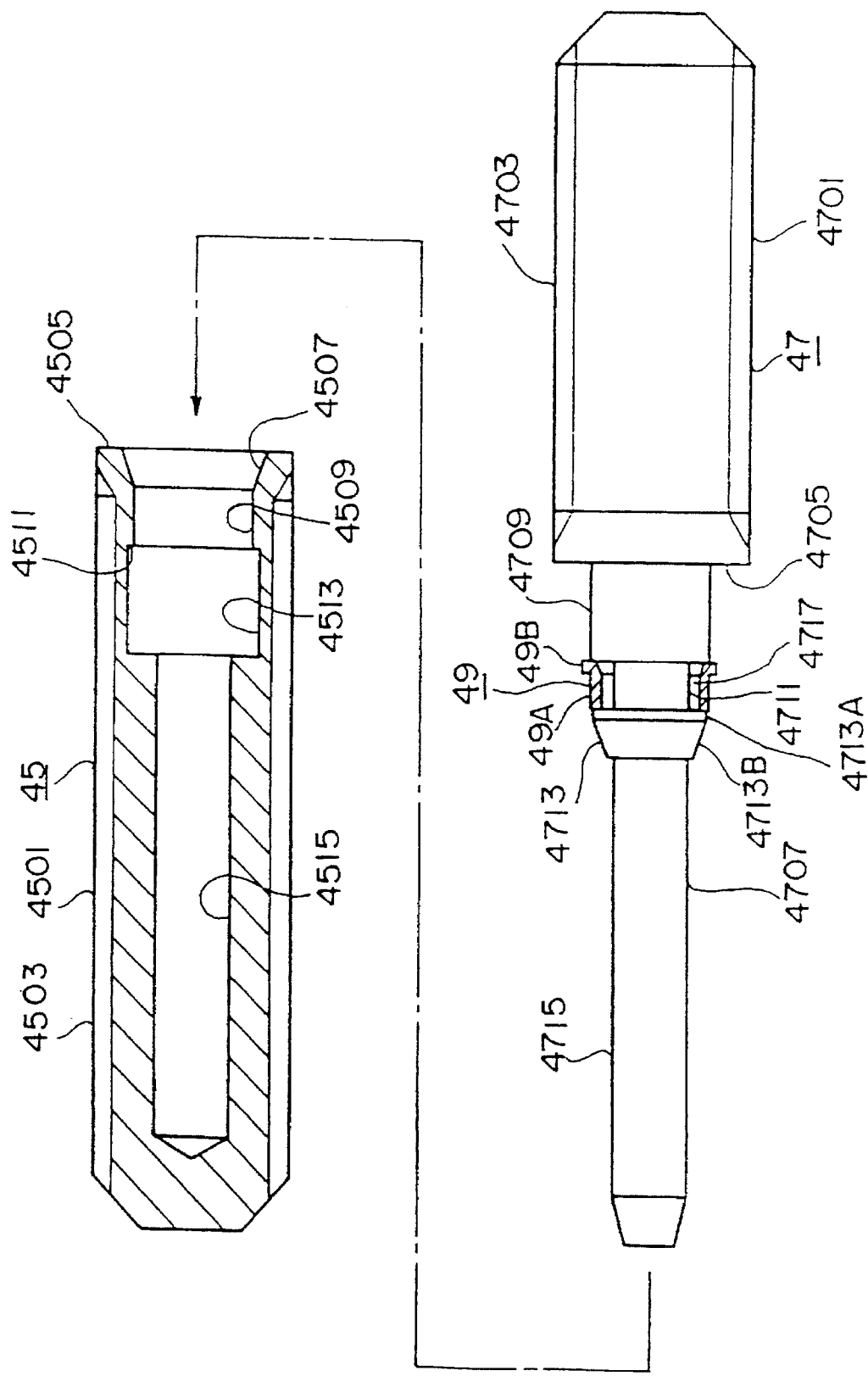
FIG. 8 is a side elevation view of first and second joints of a bone connector according to a fourth embodiment of the present invention.
Figure 9A:
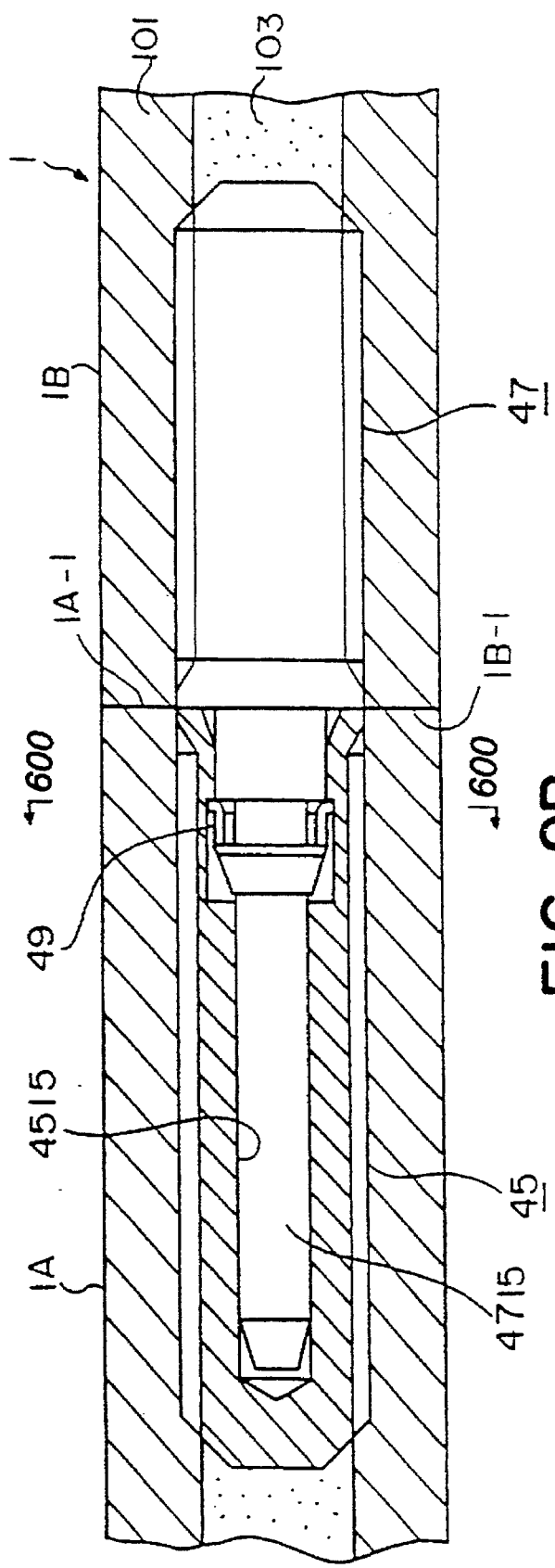
FIG. 9A is a side elevation view of first and second joints of a bone connector in an assembled state, according to a fourth embodiment of the present invention.

FIGS. 8 and 9 show a fourth embodiment of the present invention.

The first joint 45 has a bottomed hollow cylindrical body 4501 of predetermined length which is provided on the outer peripheral surface thereof with a threaded portion (male screw) 4503. The cylindrical body 3501 has an annular flat end surface 4505 which is flush with the flat end surface 1A-1 of the first bone piece 1A when the first joint 45 is fitted in the first bone piece 1A. The other end of the first joint 45 is tapered. The cylindrical body 4501 is provided on the open end thereof with a coaxial circular hole 4509 with a tapered opening 4507. The cylindrical body 4501 is also provided therein with a larger diameter circular hole (intermediate circular hole) 4513 which is connected to the small circular hole 4509 through a shoulder portion 4511, and an innermost bottomed circular hole 4515 having a predetermined length (depth) and connected to the intermediate circular hole 4513. The diameter of the innermost circular hole 4515 is smaller than the diameters of the circular holes 4513 and 4509. The circular holes 4509 and 4513 and the shoulder portion 4511 constitute an engaging portion of the first joint 45.

The second joint 47 has a circular rod body 4701 of predetermined length which is provided on the outer peripheral surface thereof with a threaded portion (male screw) 4703. The rod body 4701 has an annular flat end surface 4705 on one end on which a stepped shaft 4707 is provided. The annular flat end surface 4705 of the rod body 4701 is flush with the flat end surface 1B-1 of the second bone piece 1B when the second joint 47 is fitted in the second bone piece 1B. The other end of the rod body 4701 is conically tapered.

The stepped shaft 4707 includes a first shaft portion 4709 which is connected to the flat end surface 4705 and which can be fitted in the circular hole 4509 of the first joint, a second shaft portion 4711 which is connected to the front end of the first shaft portion 4709 and has a diameter smaller than the first shaft portion 4709, a third shaft portion 4713 connected to the front end of the second shaft portion 4711, and a fourth shaft portion 4715 which is connected to the front end of the third shaft portion 4713 and which can be fitted in the circular hole 4515.

The third shaft portion 4713 consists of a cylindrical portion 4713A having a diameter larger than the second shaft portion 4711 and connected to the latter, and a conical portion 4713B connected to the cylindrical portion 4713A. The end face of the cylindrical portion 4713A, the peripheral surface of the second shaft portion 4711, and the end face of the first shaft portion 4709 define an annular recess 4717 in which a spring member 49 is provided. The spring member 49 comprises an engaging portion of the second joint 47.

Figure 9B:
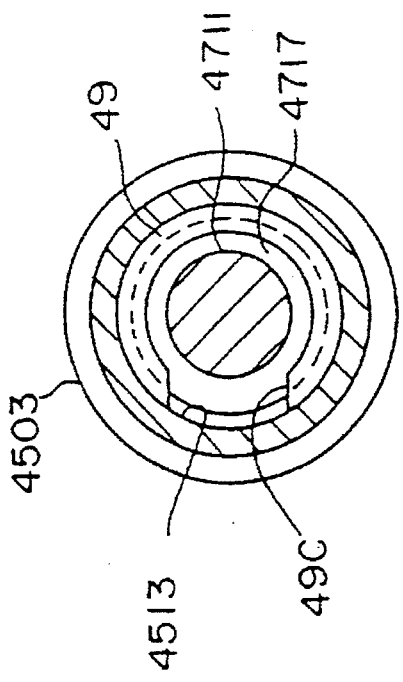
FIG. 9B is a sectional view taken along the line 600—600 in FIG. 9A.

The spring member 49 includes a cylindrical portion 49A, a flange portion 49B whose diameter is larger than the diameter of the first shaft portion 4709, and an axial opening (slit) extending through the cylindrical portion 49A and the flange portion 49B, as shown in FIG. 9B. The axial opening 49C permits the spring member to be elastically deformed to contract or expand.

The spring member 49 is preferably made of titanium, stainless steel, a titanium alloy, HDP (high density polyethylene), or high polymer polyethylene, etc.

The dimensions of the first and second joints 45, 47 and the spring member 49 are such that the flange portion 49B which has been elastically deformed or contracted during the insertion of the shaft 4707 of the second joint 47 in the circular holes 4509, 4513 and 4515 of the first joint 45 is restored to its original shape due to elastic restoring force and is snugly fitted in the intermediate circular hole 4513 to abut against the shoulder portion 4511. In this state, the surfaces 4505 and 4705 of the first and second joints 45 and 47 are flush with each other.

According to the fourth embodiment shown in FIGS. 8 and 9, in addition to the technical effects expected in the first and second embodiments, the first and second joints 45 and 47 can be coaxially held along a line by the engagement of the fourth shaft portion 4715 and the circular hole 4515 and the engagement of the first shaft portion 4709 and the circular hole 4509, and accordingly, the first and second bone pieces 1A and 1B can be accurately aligned, thus resulting in an optimal recovery of the ribs.

FIGS. 10 and 11 show a fifth embodiment of the present invention.

The first joint 55 has a bottomed hollow cylindrical body 5501 of predetermined length which is provided on the outer peripheral surface thereof with a threaded portion (male screw) 5503. The cylindrical body 5501 has an annular flat end surface 5505 which is flush with the flat end surface 1A-1 of the first bone piece 1A when the first joint 55 is fitted in the first bone piece 1A. The other end of the first joint 55 is tapered. The cylindrical body 5501 is provided on the open end thereof with a coaxial circular hole 5509 with a tapered opening 5507. The cylindrical body 5501 is also provided therein with a larger diameter circular hole (intermediate circular hole) 5513 which is connected to the small circular hole 5509 through a shoulder portion 5511, and an innermost bottomed circular hole 5515 having a predetermined length (depth) and connected to the intermediate circular hole 5513. The diameter of the innermost circular hole 5515 is smaller than the diameters of the circular holes 5513 and 5509. The circular holes 5509 and 5513 and the shoulder portion 5511 constitute an engaging portion of the first joint 55.

The second joint 57 has a circular rod body 5701 of predetermined length which is provided on the outer peripheral surface thereof with a threaded portion (male screw) 5703. The rod body 5701 has an annular flat end surface 5705 on one end on which a stepped shaft 5707 is provided. The annular flat end surface 5705 of the rod body 5701 is flush with the flat end surface 1B-1 of the second bone piece 1B when the second joint 57 is fitted in the second bone piece 1B. The other end of the rod body 5701 is conically tapered.

The stepped shaft 5707 includes a first shaft portion 5709 which is connected to the flat end surface 5705 and which can be fitted in the circular hole 5509 of the first joint, and a second shaft portion 5711 which is connected to the front end of the first shaft portion 5709 and has a diameter smaller than the first shaft portion 5709. The first shaft portion 5709 is provided on a part of the outer peripheral surface thereof with an axial recess 5713 in which a spring member 59 is provided. The spring member 59 constitutes an engaging portion of the second joint 57.

Figure 12A:
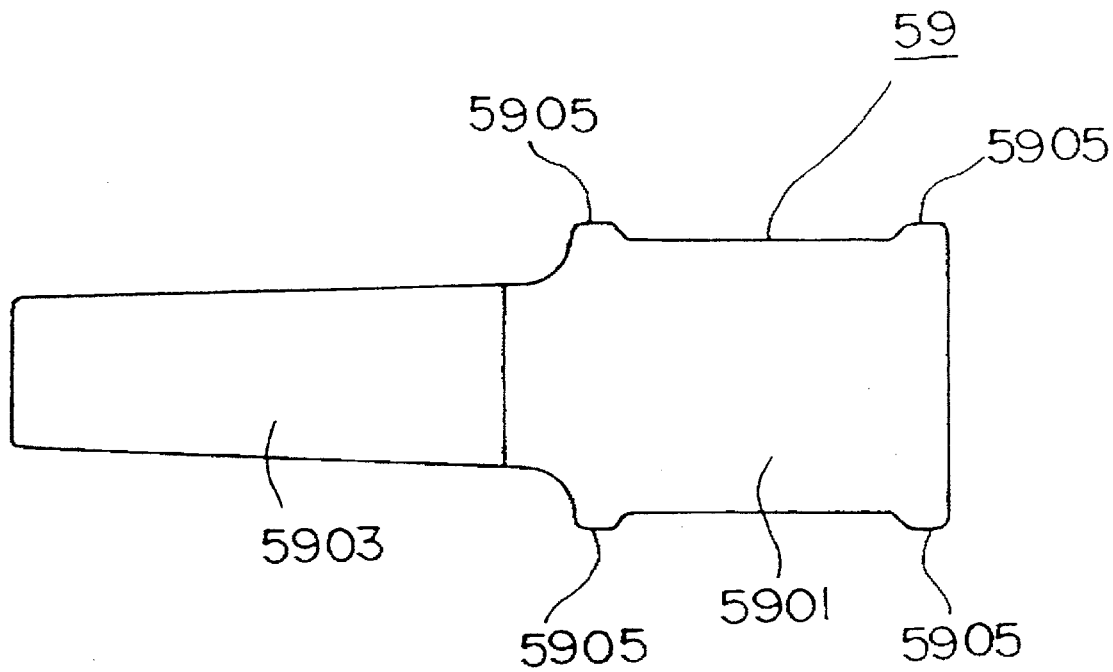
Figure 12B:
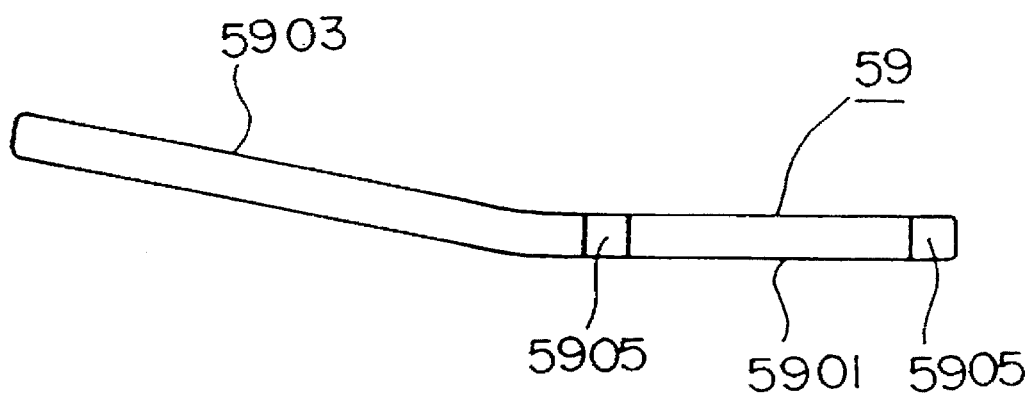

The spring member 59 includes a base plate portion 5901 which is fitted on and secured to the bottom of the recess 5713, and an oblique plate portion 5903 which extends from the base plate portion 5901 at a predetermined inclination angle. The base plate portion 5901 is provided on opposite sides thereof with projections 5905 (FIG. 12) which are snugly fitted in the recess 5713. The front end of the oblique plate portion 5903 projects out of the outer peripheral surface of the first shaft portion 5709 in the radial direction when the base plate portion 5901 is disposed on the bottom of the recess 5713.

The spring member 59 is preferably made of titanium, stainless steel, a titanium alloy, HDP (high density polyethylene), or high polymer polyethylene, etc.

The dimensions of the first and second joints 55, 57 and the spring member 59 are such that when the insertion of the shaft 5707 of the second joint 57 in the circular holes 5509, 5513 and 5515 of the first joint 55, the oblique plate portion 5903 of the spring member 59 is fitted in the circular hole 5513 of the first joint 55 and abuts against the shoulder portion 5511. In this state, the surfaces 5505 and 5705 of the first and second joints 55 and 57 are flush with each other.

According to the fifth embodiment shown in FIGS. 10 and 11, in addition to the technical effects expected in the first and second embodiments, the first and second joints 55 and 57 can be coaxially held along a line by the engagement of the second shaft portion 5711 and the circular hole 5515 and the engagement of the first shaft portion 5709 and the circular hole 5509, and accordingly, the first and second bone pieces 1A and 1B can be accurately aligned, thus resulting in an optimal recovery of the ribs.

In the first through fifth embodiments mentioned above, the first and second joints are secured to the first and second bone pieces 1A and 1B by the male threads provided on the first and second joints. The threads (screws) ensure an easy and certain connection with the bone pieces, but the connecting means is not limited to the threads (screws) in the present invention. For instance, it is possible to provide projections or the like which can be fitted in the bone pieces, on the outer peripheral surfaces of the first and second joints.

The bones to which the present invention can be applied are not limited to the ribs, and can be, for example, those of the fingers.

Although the first and second joints are made of a metal, or a ceramic, and preferably a titanium alloy and are coated with calcium phosphate compound (e.g., hydroxyapatite), the coating is not always necessary. Note that in the case that the first and second joints are coated with calcium phosphate compound, it is not necessary to coat the portions of the joints, such as the engaging portions, that are not brought into contact with the bones, since bone bonding does not take place there.

As can be understood from the above discussion, according to the present invention, the bone connector is comprised of a first joint which is embedded and secured in one of the bone pieces to be interconnected and a second joint which is embedded and secured in the other bone piece and which can be connected to the first joint. The first and second joints are made of a material strong enough to hold the cut ends of the opposed bone pieces in a close surface contact. At least the outer surfaces of the first and second joints are assimilable to the body. Consequently, in the bone connector according to the present invention, the cut ends of the bone pieces can be easily interconnected and there is no problem with the assimilation to or bioactive affinity with the body. In particular, the bone connector according to the present invention can be advantageously used to connect the cut ends of a long bone which has been cut at an intermediate portion thereof.

We claim:

1. A bone connector comprising:

a first joint which is adapted to be inserted and secured in one of two cut bone pieces to be interconnected at the cut end thereof, said first joint comprising a substantially cylindrical body having a predetermined diameter and threads surrounding a peripheral surface thereof for screw engaging in the cortical bone of one of the two cut bone pieces, and a substantially flat end surface which is adapted to be substantially flush with the cut end of one of the two cut bone pieces, the cut end substantially encircling said substantially flat end surface upon insertion of said first joint;

a second joint which is adapted to be inserted and secured in the other of the two cut bone pieces at the cut end thereof, said second joint comprising a substantially cylindrical body having a diameter substantially equal to said predetermined diameter and threads surrounding a peripheral surface thereof for screw engaging in the cortical bone of one of the two cut bone pieces, and a substantially flat end surface which is adapted to be substantially flush with the cut end of the other of the two cut bone pieces, the cut end substantially encircling said substantially flat end surface of said second joint upon insertion of said second joint;

said first joint further comprising a stepped engaging groove extending through said substantially flat end surface in a direction substantially perpendicular to a longitudinal axis of said substantially cylindrical body, wherein said stepped engaging groove comprises a first groove having a first width meeting said substantially flat end surface, and a second groove having a second width greater than said first width, said second groove positioned within said cylindrical body and extending from said first groove; and said second joint further comprising a pair of engaging projections fixed to and extending from said substantially flat end surface, wherein each said engaging projection comprises a leg portion substantially perpendicular to said substantially flat end surface and engageable with said first groove, and a projection which projects substantially perpendicularly from said leg portion and is engageable with said second groove, wherein said engaging projections engage with said stepped engaging groove to retain said substantially flat end surfaces in contact with one another.

2. A bone connector according to claim 1, wherein said substantially flat end surfaces are adapted to be located flush with respective end surfaces of the two cut bone pieces to be interconnected when said threaded portions are screwed into the cortical bone portions of the two cut bone pieces to be interconnected.

3. A bone connector according to claim 1, wherein at least outer surface portions of said first and second joints are made of a material having bioactive affinity with the body.

4. A bone connector according to claim 3, wherein said material having bioactive affinity is a calcium phosphate compound.

5. A bone connector according to claim 1, wherein said first and second joints are made of a material selected from the group consisting of titanium, stainless steel, and titanium alloys.

6. A bone connector according to claim 5, wherein said first and second joints are coated with a material having an affinity with the body.

7. A bone connector according to claim 1, wherein said first and second joints are adapted to be implanted in a lengthwise direction of the two cut bone pieces, and said first and second joints are adapted to remain implanted after healing of the cut bone pieces.

8. A bone connector according to claim 1, wherein said first and second joints comprise intramedullary implants.

9. A bone connector according to claim 1, wherein linear movement of said first and second joints toward one another is sufficient to engage said engaging projections with said stepped engaging groove.

10. A bone connector according to claim 1, wherein said engaging projections are adapted to be engaged with said engaging groove when said first and second joints are fully screw engaged into the two cut bone pieces, so as to be substantially flush therewith.

11. A bone connector according to claim 1, wherein said first joint is prevented from rotating with respect to said second joint, upon engagement of said engaging projections with said engaging groove.

12. A bone connector comprising:

first and second joints having a substantially circular cross-section wherein each said cross-section is substantially equal to the other in diameter, said first and second joints being adapted to be secured to cut ends of bone pieces to be interconnected;

said first and second joints each comprising threads surrounding a peripheral surface thereof for screw engaging in the cortical bone of one of the two cut bone pieces, and wherein one of said first and second joints comprises a stepped engaging groove extending through an end surface thereof in a direction substantially perpendicular to a longitudinal axis of said one of said first and second joints, wherein said stepped engaging groove comprises a first groove having a first width meeting said end surface, and a second groove having a second width greater than said first width, said second groove positioned within said one of said first and second joints and extending from said first groove;

the other of said first and second joints comprises a pair of engaging projections fixed to and extending from an end surface of said other of said first and second joints, wherein each said engaging projection comprises a leg portion substantially perpendicular to said end surface and engageable with said first groove, and a projection which projects from said leg portion and is engageable with said second groove, wherein said engaging projections engage with said stepped engaging groove to retain said end surfaces of said first and second joints in contact with one another; and wherein upon engaging said engaging projections with said stepped engaging groove to retain said end surfaces of said first and second joints in contact with one another, said first and second joints are adapted to maintain the cut ends of bone pieces in contact, such that the cut ends substantially encircle said end surfaces of said first and second joints.

13. A bone connector according to claim 12, further comprising:

means for elastically deforming said engaging protections upon insertion thereof into said stepped engaging groove, wherein the deformation of said engaging projections is restored upon engagement of said engaging projections with said stepped engaging groove, wherein the restoration of the deformation locks the engagement of said engaging projections.

14. A bone connector according to claim 13, wherein said leg portions integrally connect said projections, respectively, with said end surface of said other of said first and second joints, and wherein said end surface of said other of said first and second joints comprises a substantially flat end surface adapted to fit substantially flush with the cut end of one of the bone pieces upon insertion therein.

15. A bone connector according to claim 12, wherein said first and second joints comprise intramedullary implants.

16. A bone connector according to claim 12, wherein linear movement of said first and second joints toward one another is sufficient to engage said engaging projections with said stepped engaging groove.

17. A bone connector according to claim 12, wherein said first joint comprises a substantially cylindrical body and said threads of said first joint surround said substantially cylindrical body of said first joint; and wherein said second joint comprises a substantially cylindrical body and said threads of said second joint surround said substantially cylindrical body of said second joint.

18. A bone connector according to claim 12, wherein said engaging projections are adapted to be engaged with said engaging groove when said first and second joints are fully screw engaged into the two cut bone pieces, so as to be substantially flush therewith.

19. A bone connector according to claim 12, wherein said first joint is prevented from rotating with respect to said second joint, upon engagement of said engaging projections with said engaging groove.

20. A bone connector comprising:

a first joint which is adapted to be secured to a cut end of one of two bone pieces to be interconnected; and a second joint which is adapted to be secured to a cut end of the other of the two bone pieces;

said first joint provided with a first body having external threads wherein said first joint can be screwed and secured intramedullarly in the cut end of the one bone piece, said first body comprising a stepped engaging groove extending through an end surface thereof in a direction substantially perpendicular to a longitudinal axis of said first body, wherein said stepped engaging groove comprises a first groove having a first width meeting said end surface, and a second groove having a second width greater than said first width, said second groove positioned within said first body and extending from said first groove, wherein said end surface of said first body comprises a substantially flat end which is adapted to be substantially flush with the cut end of the one bone piece, the cut end substantially encircling said substantially flat end surface upon implantation of said first joint;

said second joint being provided with a second body having external threads wherein said second joint can be screwed and secured intramedullarly in the cut end of the other bone piece, said second body comprising a pair of engaging projections fixed to and extending from an end surface of said second body, wherein each said engaging projections comprises a leg portion substantially perpendicular to said end surface and engageable with said first groove, and a projection which projects from said leg portion and is engageable with said second groove, wherein said engaging projections engage with said stepped engaging groove to retain said end surfaces of said first and second joints in contact with one another, wherein said end surface of said second body comprises a substantially flat end which is adapted to be substantially flush with the cut end of the other bone piece, the cut end substantially encircling said substantially flat end surface of said second joint upon implantation of said second joint;

wherein engagement of said engaging projections in said stepped engaging groove is adapted to maintain the cut ends of the bone pieces flush to each other;

said first and second joints being made of a material strong enough to hold the flush contact of the cut ends of the bone pieces.

21. A bone connector according to claim 20, wherein said first and second bodies are coated at least at the outer surfaces thereof with a material having a bioactive affinity with the body.

22. A bone connector according to claim 20, wherein said engaging projections are integral with said substantially flat end of said second body.

23. A bone connector according to claim 20, wherein linear movement of said first and second joints toward one another is sufficient to engage said engaging projections with said stepped engaging groove.

24. A bone connector according to claim 20, wherein said first joint comprises a substantially cylindrical body and said threads of said first joint surround said substantially cylindrical body of said first joint; and wherein said second joint comprises a substantially cylindrical body and said threads of said second joint surround said substantially cylindrical body of said second joint.

25. A bone connector according to claim 20, wherein said engaging projections are adapted to be engaged with said engaging groove when said first and second joints are fully screw engaged into the two cut bone pieces, so as to be substantially flush therewith.

26. A bone connector according to claim 20, wherein said first joint is prevented from rotating with respect to said second joint, upon engagement of said engaging projections with said engaging groove.

* * * * *